(12) United States Patent
Jojic et al.

(10) Patent No.: US 8,706,421 B2
(45) Date of Patent: Apr. 22, 2014

(54) SHIFT-INVARIANT PREDICTIONS

(75) Inventors: Nebojsa Jojic, Redmond, WA (US);
David E. Heckerman, Bellevue, WA (US); Noah Aaron Zaitlen, Venice, CA (US); Manuel Jesus Reyes Gomez, Kirkland, WA (US)

(73) Assignee: Microsoft Corporation, Redmond, WA (US)

( * ) Notice: Subject to any disclaimer, the term of this patent is extended or adjusted under 35 U.S.C. 154(b) by 1341 days.

(21) Appl. No.: 11/738,411

(22) Filed: Apr. 20, 2007

(65) Prior Publication Data

US 2007/0192039 A1    Aug. 16, 2007

Related U.S. Application Data

(63) Continuation-in-part of application No. 11/356,196, filed on Feb. 16, 2006, now abandoned.

(51) Int. Cl.
*G01N 33/48* (2006.01)
*G06F 19/18* (2011.01)

(52) U.S. Cl.
CPC ................................ *G06F 19/18* (2013.01)
USPC .......................................................... 702/19

(58) Field of Classification Search
CPC ... G06F 17/30; G06F 17/30994; G06F 19/16; G06F 19/18; G06F 19/20; G06F 19/22; G06F 19/24; G06F 19/704; G06F 19/707; G06F 7/00
USPC .......................................................... 702/19
See application file for complete search history.

(56) References Cited

U.S. PATENT DOCUMENTS

| | | | |
|---|---|---|---|
| 5,933,819 | A | 8/1999 | Skolnick et al. |
| 6,861,234 | B1 | 3/2005 | Simard et al. |
| 6,895,396 | B2 | 5/2005 | Schwartz et al. |
| 7,094,555 | B2 | 8/2006 | Kwok et al. |
| 2004/0072162 | A1 | 4/2004 | Fomsagaard et al. |
| 2004/0072246 | A1 | 4/2004 | Martin et al. |
| 2004/0072249 | A1 | 4/2004 | Hoffman et al. |
| 2004/0137537 | A1 | 7/2004 | Montero-Julian et al. |
| 2005/0074809 | A1 | 4/2005 | Brusic |
| 2005/0074813 | A1 | 4/2005 | Nauss et al. |
| 2005/0079549 | A1 | 4/2005 | Castracane |
| 2005/0095655 | A1 | 5/2005 | Montero-Julian et al. |
| 2006/0057673 | A1 | 3/2006 | Liu et al. |
| 2006/0084116 | A1 | 4/2006 | Muchhal |
| 2006/0111554 | A1 | 5/2006 | Lasters et al. |
| 2006/0160071 | A1 | 7/2006 | Heckerman et al. |
| 2006/0257944 | A1 | 11/2006 | Fridman et al. |
| 2007/0005262 | A1 | 1/2007 | Gershoni et al. |
| 2007/0154953 | A1 | 7/2007 | Brunner et al. |

FOREIGN PATENT DOCUMENTS

| | | |
|---|---|---|
| WO | W09859244 A1 | 12/1998 |
| WO | WO 0220564 A2 | 3/2002 |
| WO | 2005038429 A2 | 4/2005 |

OTHER PUBLICATIONS

Swain et al. (Bioinformatics and Bioengineering Conference, 2001. Proceedings of the IEEE 2nd Int. Symposium on Nov. 4-6, 2001 pp. 81-88).*
Nielsen et al. (Protein Science (2003), 12:1007-1017.).*
Mamitsuka (Proteins: Structure, Function, and Genetics 33:460-474 (1998)).*
Zhang et al. (Protein Science (1997). 6:1057-1064).*
Freire (Pure & Appl. Chem., vol. 69, No. 11, pp. 2253-2261, 1997).*
Kratochwil, Nicole A. et al. Predicting plasma protein binding of drugs: a new approach. Biochemical Pharmacology. Nov. 1, 2002, vol. 64, Issue 9, pp. 1355-1374.
Holmes, I. et al. An expectation maximization algorithm for training hidden substitution models. Journal of Molecular Biology. Apr. 12, 2002, vol. 317, Issue 5, pp. 753-764.
International Search Report and Written Opinion dated Oct. 9, 2008 for PCT Application Serial No. PCT/US2008/060945, 11 Pages.
Miyazawa, et al., J. Mol. Biol., vol. 256, p. 623-644, 1996.
Specific weight. (1992). In Academic Press Dictionary of Science and Technology. Retrieved Jun. 25, 2008, from http://www.credoreference.com/entry/3161132.
Density. (1992). In Academic Press Dictionary of Science and Technology. Retrieved Jun. 25, 2008, from http://www.credoreference.com/entry/3094286.
OA mailed Jul. 7, 2008 for U.S. Appl. No. 11/356,196, 22 pages.
Brusic, et al. "Prediction of MHC Binding Peptides Using Artificial Neural Networks", Complexity International, Apr. 1995, vol. 02, http://www.complexity.org.au/ci/vol02/vbb/vbb.html, last accessed Jan. 24, 2007, 10 pages.
Peters, et al. "A Community Resource Benchmarking Predictions of Peptide Binding to MHC-I Molecules", http://mhcbindingpredictions.immuneepitope.org/manuscript.pdf, accessed Jan. 24, 2007, 51 pages.

(Continued)

*Primary Examiner* — Jerry Lin
(74) *Attorney, Agent, or Firm* — Stephen A. Wight; Carole Boelitz; Micky Minhas

(57) ABSTRACT

Shift invariant predictors are described herein. By way of example, a system for predicting binding information relating to a binding of a protein and a ligand can include a trained binding model and a prediction component. The trained binding model can include a hidden variable representing an unknown alignment of the ligand at a binding site of the protein. The prediction component can be configured to predict the binding information by employing information about the protein's sequence, the ligand's sequence and the trained binding model.

14 Claims, 5 Drawing Sheets

(56) References Cited

OTHER PUBLICATIONS

Yanover, et al. "Predicting Protein-Peptide Binding Affinity by Learning Peptide-Peptide Distance Functions", Predicting Binding Affinity by Learning Distance Functioning, pp. 456-471, last accessed Jan. 24, 2007.
Zhu, et al. "Improving Prediction of MHC Class I Binding Peptides with Additional Binding Data", https://www.jsbi.org/journal/GIW04/GIW04P127.pdf, last accessed Jan. 24, 2007, 2 pages.
Hertz, et al. PepDist: a new framework for protein-peptide binding prediction based on learning peptide distance functions. BMC Bioinformatics. Mar. 20, 2006;7 Suppl 1:S3.
Sette, et al. Nine major HLA class I supertypes account for the vast preponderance of HLA-A and -B polymorphism, Immunogenetics, Nov. 1999 50:201-212.
Jones, et al. "A new approach to protein fold recognition," Nature (1992) 358:86-89.
Melo, et al. "Statistical potentials for fold assessment," Protein Science (2002) 11:430-448.
Chang, et al. Predicting peptides bound to I-Ag7 class II histocompatibility molecules using a novel expectation-maximization alignment algorithm. Proteomics 2007, 7, 367-377.
Jojic, et al. "Topographic transformation as a discrete latent varaible," Neural Information Processing Systems (NIPS) '99,Nov. 1999, Denver, CO.
Stern, et al. Peptide 15-mers of defined sequence that substitute for random amino acid copolymers in amelioration of experimental autoimmune encephalomyelitis. Proc Natl Acad Sci U S A. Feb. 1, 2005;102(5):1620-5. Epub Jan. 21, 2005.
Karpenko, et al. Prediction of MHC class II binders using the ant colony search strategy. Artif Intell Med. Sep.-Oct. 2005;35(1-2):147-56.
Reche, et al. Enhancement to the RANKPEP resource for the prediction of peptide binding to MHC molecules using profiles. Immunogenetics. Sep. 2004;56(6):405-19. Epub Sep. 3, 2004.
Nielsen, et al. Improved prediction of MHC class I and class II epitopes using a novel Gibbs sampling approach. Bioinformatics. Jun. 12, 2004;20(9):1388-97. Epub Feb. 12, 2004.
Davies, et al. A novel predictive technique for the MHC class II peptide-binding interaction. Mol Med. Sep.-Dec. 2003;9(9-12):220-5.
Murugan, et al. Prediction of MHC class II binding peptides based on an iterative learning model. Immunome Res. Dec. 13, 2005;1:6.
Brusic, et al. Prediction of MHC class II-binding peptides using an evolutionary algorithm and artificial neural network. Bioinformatics. 1998;14(2):121-30.
N. Jojic, et al., "Using "epitomes" to model genetic diversity: Rational design of HIV vaccine cocktails,", in Advances in Neural Information Processing Systems 18, Presented at NIPS 2005, 8 pages.
O. Schueler-Furman, et al., "Structure-based prediction of binding peptides to MHC class I molecules: Application to a broad range of MHC alleles," Protein Science, 2000, pp. 1838-1846, vol. 9.
A. Sette, et al., "Peptide binding to the most frequent HLA-A class I alleles measured by quantitative molecular binding assays," Molecular Immunology, 1994, pp. 813-822, vol. 31, No. 11.
M. Bhasin, et al., "MHCBN: A comprehensive database of MHC binding and non binding peptides," Bioinformatics, 2003, pp. 665-666, vol. 19, No. 5.
H. Rammensee, et al., "SYFPEITHI: database for MHC ligands and peptide motifs," Immmunogenetics, 1999, pp. 213-219, vol. 50.
C. Moore, et al., "Evidence of HIV-1 Adaptation to HLA-Restricted Immune Responses at a Population Level," Science, May 24, 2002, pp. 1439-1443, vol. 296.
C. Yanover, et al., "Predicting protein-peptide binding affinity by learning peptide-peptide distance functions," Recomb, 2005, pp. 456-471.
K. Arien, et al., "Replicative fitness of historical and recent HIV-1 isolates suggest HIV-1 attenuation over time," AIDS, Oct. 14, 2005, pp. 1555-1564, vol. 19.
N. Jojic, et al., "Learning MHC I-peptide binding", Bioinformatics, vol. 22 No. 14 2006, pp. e227-e235.

H. Singh, et al., "ProPred: prediction of HLA-DR binding sites", Bioinformatics Applications Note, vol. 17, No. 12, 2001, pp. 1236-1237.
Altuvia et al. (1997). Human Immunology, vol. 58, pp. 1-11.
Wojciechowski et al. (2001). J. Comput. Chem., vol. 23, pp. 189-197.
Lee, et al. Biophysical Chemistry, vol. 115, p. 209-214. Jan. 6, 2005.
Deng, et al. J. Chem. Inf. Comput. Sci. vol. 44, pp. 699-703, 2004.
Park, et al. Proteins, vol. 40, pp. 237-248. 2000.
Marshall, et al. Proteomics and Protein-Protein Interactions: Biology chemistry, bioinformatics and Drug Design, Chapter 2, pp. 115-146. 2005.
Altuvia, et al. Methods, vol. 34, pp. 454-459. 2004.
Wiesmuller, et al. Biol. Chem. vol. 382, pp. 571-579. 2001.
Lazaridis et al., "Effective Energy Functions for Protein Structure Prediction", Theory and Simulation, http://www.sci.ccny.cuny.edu/~themis/curropin.pdf, last accessed Jan. 24, 2007, 7 pages.
Lilien, et al. "A Novel Ensemble Based Scoring and Search Algorithm for Protein Redesign, and Its Application to Modify the Substrate Specificity of the Gramicidin Synthetase a Phenylalanine Adenylation Enzyme", http://delivery.acm.org/10.1145/980000/974622/p46-lilien.pdf?key1=974622&key2=3858269611&coll=GUIDE&dl=GUIDE&CFID=75919783&CFTOKEN=92791909, last accessed Jan. 24, 2007, 12 pages.
Zhao, et al. "Application of Support Vector Machines for T-cell Epitopes Prediction", Bioinformatics, Apr. 7, 2003, vol. 19 No. 15 2003, pp. 1978-1984, http://bioinformatics.oxfordjournals.org/cgi/reprint/19/15/1978, last accessed Jan. 24, 2007, 7 pages.
Guler, "A Model With an Intrinsic Property of Learning Higher Order Correlations", Neural Networks, vol. 14, 2001, pp. 495-504.
Neal, "NIPS (Neural Information Processing Systems)", NIPS 2004 Conference, Dec. 2004.
Brusic, et al., "Prediction of Promiscuous Peptides that Bind HLA Class I Molecules", Immunology and Cell Biology, 2002, vol. 80, Issue 3, pp. 280-285.
Heckerman, et al., "Leveraging Information Across HLA Alleles/Supertypes Improves Epitope Prediction", Springer Berlin/Heidelberg, Research in Computational Molecular Biology, Lecture Notes in Computer Science, 2006, vol. 3909, pp. 296-308.
International Search Report and Written Opinion dated Oct. 9, 2008 for PCT Application Serial No. PCT/US20081060945, 11 Pages.
Jacob, et al., "Epitope Prediction Improved by Multitask Support Vector Machines", Retrieved on Feb. 6, 2007, Available at <<http://hal.archives-ouvertes.fr/docs/00/12/90/62/PDF/mtkepitope-jacob-vert.pdf>>, 18 pgs.
Jain, "Scoring Noncovalent Protein-Ligand Interactions: A Continuous Differentiable Function Tuned to Compute Binding Affinities", Springer Netherlands, Journal of Computer-Aided Molecular Design, 1996, vol. 10, No. 5, pp. 427-440.
Jurs, et al., "Studies of Chemical Structure-Biological Activity Relations Using Pattern Recognition", ACS Symposium Series, 1979, vol. 112, Computer-Assisted Drug Design, Chapter 4, pp. 103-129.
Lee, et al., "Learning With Positive and Unlabeled Examples Using Weighted Logistic Regression", In the Proceedings of the Twentieth International Conference on Machine Learning, 2003, 8 pgs.
Qu, et al., "Bayesian Protein Family Classifier", AAAI Press, In the Proceedings of the 6th International Conference on Intelligent Systems for Molecular Biology, 1998, pp. 131-139 (9 pgs.).
Rousseeuw, et al., "Robustness Against Separation and Outliers in Logistic Regression", Elsevier Science Publishers B.V., Computational Statistics & Data Analysis, 2003, vol. 43, Issue 3, pp. 315-332.
Tandon, et. al., "Predicting Continuous Epitopes in Proteins", IEEE, In the Proceedings of the Computational Systems Bioinformatics Conference, 2005, pp. 133-134 (2 pgs.).
Williams, et al., "Incomplete-Data Classification Using Logistic Regression", ACM, In the Proceedings of the 22nd International Conference on Machine Learning, 2005, pp. 972-979.
Xiao, et al., "Prediction of Genomewide Conserved Epitope Profiles of HIV-1: Classifier Choice and Peptide Representation", Statistical Applications in Genetics and Molecular Biology, 2005, vol. 4, Issue 1, Article 25, 36 pgs.

(56) References Cited

OTHER PUBLICATIONS

Bilenko, et al., "Adaptive Duplicate Detection Using Learnable String Similarity Measures", In the Proceedings of the Ninth ACM SIGKDD International Conference on Knowledge Discovery and Data Mining, 2003, pp. 39-48.

Chakrabarti, et al., "Dissecting Protein-Protein Recognition Sites", Wiley-Liss Inc., Proteins: Structure, Function, and Bioinformatics, vol. 47, Issue 3, May 2002, pp. 334-343.

Mallios, "Predicting Class II MHC/Peptide Multi-level Binding with an Iterative Stepwise Discriminant Analysis Meta-algorithm", Oxford University Press, Bioinformatics, vol. 17, No. 10, 2001, pp. 942-948.

Bhasin et al., "Pcleavage: an SVM based method for prediction of constitutive preteasome and immunoproteasome cleavage sites in antigenic sequences", Nucleic Acids Research, 2005. vol. 33, Web Server issue, 6 pages.

Espadaler et al., "Prediction of protein-protein interations using distant conservation of sequence patterns and structure relationships", Bioinformatics, vol. 21, No. 16, 2005, pp. 3360-pp. 3368.

Florea, et al., "Epitope Prediction Algorithms for Peptide-based Vaccine Design", Computer Society, In the Proceedings of the Computational Systems bioinformatics, 2003, 10 pages.

Gotoh, "Multiple Sequence Alignment: Algorithms and Applications", Advanced Biophysics, 1999, vol. 36, pp. 159-206.

Lund, et al., "Definition of Supertypes for HLA Molecules Using Clustering of Specificity Matrices", Immunogenetics, vol. 55, No. 12, 2004, pp. 797-810.

Panchenko et al., "Combination of Threading Potentials and Sequence Profiles Improves Fold Recognition", Journal of Molecular Biology 296, 2000, 13 pages.

Peters et al., "The Immune Epitope Database and Analysis Resource: From Vison to Blueprint", PLoS Biology, Mar. 2005, vol. 3, Issue 3, 3 pages.

Schmidler et al., "Bayesian Segmentation of Protein Secondary Structure", Journal of Computational Biology, vol. 7, Nos. 1/2, 2000, pp. 233-248.

Tsuda, et al., "Marginalized Kernels for Biological Sequences", Bioinformatics, 2002, vol. 18, Supplement 1, pp. S268-S275.

Waterhouse, "Classification and Regression using Mixtures of Experts", PhD. Thesis, University of Cambridge, 1997, pp. 1-pp. 215.

\* cited by examiner

SHIFT-INVARIANT PREDICTIONS

CROSS-REFERENCE TO RELATED APPLICATIONS

This application is a Continuation-in Part of U.S. patent application Ser. No. 11/356,196 filed Feb. 16, 2006, and entitled "MOLECULAR INTERACTION PREDICTORS," the entirety of which is incorporated herein by reference.

BACKGROUND

Despite significant progress over the last few years, predicting 3-D protein structure and protein-ligand binding remain difficult problems to solve. Research in this area has focused on complex physics-based models using a large number of particles to describe not only the amino acids in the proteins, but also the solvent that surrounds them.

One particular example of protein-ligand binding that is of great interest to researchers is the interaction between a Major Histocompatibility Complex (MHC) molecule and a peptide. One example of a structural model that can be used to predict peptide-MHC affinity is the threading model. The threading model is based on the premise that proteins fold in a finite number of ways and that the change in the short peptide that binds to MHC does not dramatically influence the 3-D binding configuration. Therefore, instead of screening all theoretically possible ways a particular sequence can fold and bind to another peptide to properly choose the sequence's 3-D structure, the protein binding configurations that are already known are used to compute binding energy (or affinity).

Many structures of MHC-peptide binding configurations have been obtained by crystallographers. Since x-ray crystallography reveals that MHC-peptide complexes exhibit a finite number of conformations, the threading approach can be applied to the problem of predicting MHC-peptide binding. The threading approach assumes that energy is additive, but it introduces a simplification that allows estimation of the binding energy of a peptide with an MHC molecule whose 3-D configuration of binding with some other peptide is known. In particular, the assumption is that the binding energy is dominated by the potentials of pairwise amino acid interactions that occur when the amino acids are in close proximity (e.g., distance smaller than 4.5 Å). Another assumption underlying the threading approach is that the proximity pattern of the peptide in the groove (i.e., MHC binding site) does not change dramatically with the peptide's amino acid content. As the pairwise potentials are assumed to depend only on the amino acids themselves and not on their context in the molecule, the energy becomes a sum of pairwise potentials taken from a symmetric 20×20 matrix of pairwise potentials between amino acids. These parameters are computed based on the amino acid binding physics and there are several published sets derived in different ways.

The MHC-peptide threading procedure utilizes solved MHC-peptide complexes as the threading template, a definition of interacting residues and a pairwise contact potential table. To predict MHC-peptide binding, the query sequence is "threaded" through the various known MHC structures to find the best fit. These structural data files are available, for instance, from the Research Collaboratory for Structural Bioinformatics (RCSB) Protein Data Bank (PDB). The algorithm for the threading model proceeds as follows—given a known structure of an MHC-peptide complex, the contacting MHC residues for each peptide position are determined, the amino acid-amino acid pairwise potentials are used to score the interaction of a peptide amino acid at a certain position with all its contacting residues and assuming position independence, the peptide's score is the sum of the amino acid scores.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The subject matter described herein facilitates predicting information about binding information (e.g., binding energy, binary binding event, binding probability, etc.). By way of example, the specificity of an MHC molecule binding to short peptide fragments from cellular as well as pathogenic proteins (referred to as epitopes) has been found to correlate with disease outcome and pathogen or cancer evolution. The large variation in MHC class II epitope length has complicated the training of predictors for binding information as compared to that of MHC class I predictors. In order to address this issue, the relative position of the peptide inside the MHC groove can be treated as a hidden variable and the ensemble of different binding configurations can be modeled. The model can be trained utilizing a training procedure that iterates the predictions with re-estimation of the parameters of a binding groove model. Such a model generalizes to new MHC class II alleles that were not a part of the training set. The experimental data presented below indicates that this technique outperforms other approaches to MHC II-epitope binding prediction and demonstrates that the model can be used to explain previously documented associations between MHC II alleles and disease. Thus, the predictions can be used as an alternative to laboratory experiments for example, to facilitate drug discovery.

The following description and the annexed drawings set forth in detail certain illustrative aspects of the subject matter. These aspects are indicative, however, of but a few of the various ways in which the subject matter can be employed and the claimed subject matter is intended to include all such aspects and their equivalents.

DETAILED DESCRIPTION

Figure 1:
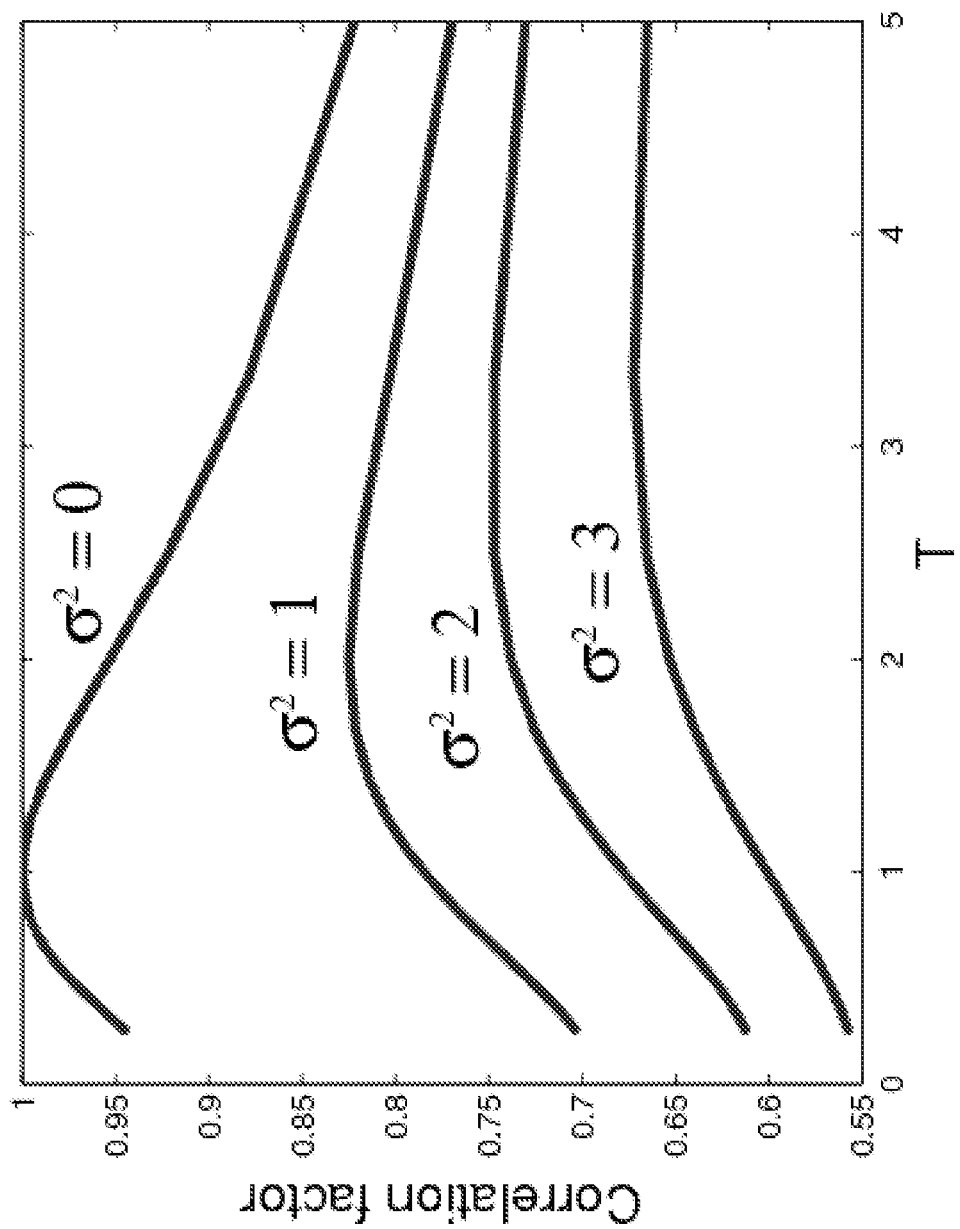
FIG. 1 is a graph showing the effect of the temperature T used in the energy estimate given by equation (8) below on the prediction accuracy measured in terms of the correlation between the estimate and the "true" energy in the synthetic experiment described below. The curves correspond to the variance of the modeling error $v^2$ of 0, 1, 2, and 3. As shown, higher error variance leads to lower Spearman correlation factors and the best correlation is achieved at optimal temperatures which increase with the error variance.

Although the subject matter described herein may be described in the context of MHC-peptide binding and a Shift Invariant Double Threading (SIDT) model, the subject matter is not limited to these particular embodiments. Rather, the techniques described herein can be applied to any suitable type of molecular binding and any suitable implementation including but not limited to a threading approach.

The interaction between an MHC molecule and a peptide can be characterized by a binding free energy. The lower the binding free energy, the greater the affinity between the two proteins. The binding free energy is the difference between the free energy of the bound and unbound states. The binding energy for an MHC-peptide complex can be directly measured by competition experiments with a standard peptide. Typically, it is expressed as the ratio between the half-maximal inhibitory concentration (IC50) of the standard peptide to that of the test peptide. In the context of MHC-peptide binding, IC50 is the concentration of the test peptide required to inhibit binding of the standard peptide to MHC by 50%. The result of such experiments is a set of relative binding energies (negative logarithms of the relative concentrations) for different MHC-peptide combinations.

The open binding pocket of the MHC class II molecules allows for a greater variation in peptide length relative to the closed pocket of the MHC class I molecules. A longer peptide (e.g., 15-30 amino acids) has only part of its sequence in the groove of an MHC class II molecule and the largest difference in the binding of peptides to the same MHC II allele occurs where the bound part of the peptides start. This difference combined with the relative lack of sequence similarity across binding peptides makes MHC II binding prediction significantly more challenging for the class II molecules. Previous MHC class II binding predictors have been focused on methods to identify a nine amino acid binding core of the peptide because this size segment is widely believed to be responsible for a majority of the binding. These techniques are then combined with one of numerous existing methods for predicting MHC class I binding over the derived nonamers.

A novel binding model that can be trained on examples of measured binding affinities for a number of allele-peptide combinations as well as on lists of good and bad binders for various alleles is described herein. One implementation of this model—the Shift Invariant Double Threading (SIDT) model—outperforms several previously published MHC class II epitope prediction techniques due to its unique treatment of the variable position of the peptide with respect to the binding groove. This particular implementation is physics-based and treats the binding configurations with different possible peptide positions as a statistical ensemble in a thermodynamic sense. The SIDT implementation, while guided by the known MHC II structures, is simplified and enriched with trainable parameters that allow it to be refined using published binding data.

As opposed to other structure-based techniques, the SIDT implementation is both accurate in binding energy prediction and computationally efficient. For instance, due to the computational cost, some binding prediction techniques report results for only small numbers of peptides. In contrast, testing a new peptide with the SIDT model takes a fraction of a second. Moreover, one of the most appealing properties of the SIDT technique is that it generalizes well to previously unseen MHC II alleles (or unseen combinations of alpha and beta chains). The experimental data presented below demonstrates the accuracy of this implementation for identifying targets and drugs for an autoimmune disorder. The model also can be used to explain certain evolutionary trends in pathogens.

Structure-based methods attempt to model the physics of MHC binding using the growing number of MHC class I and II molecules that have been solved by X-ray crystallography. By way of example, a structure-based binding model can treat the possible peptide alignments as an ensemble of possible configurations. Rather than assuming simply that any peptide alignment is equally possible, or turning to a separate methodology to provide the best alignment, the distribution over possible states can be inferred for each peptide-MHC combination based on the predicted state energy. The distribution is not treated as a distribution over a variable with mutually exclusive and exhaustive states, but as population frequencies in the thermodynamics sense, and the equivalent total binding energy is estimated accordingly. As will be explained below, this approach to MHC class II binding prediction outperforms other previously published techniques.

By way of example, a hidden random integer variable l can be used to represent the starting index of the segment of the peptide bound to the MHC groove such that $l \in [1, N-8]$, where N is the length of the peptide. The segment that is inside the groove can be assumed to be of various lengths, e.g., 9 or 8-11 amino acids long. Other hidden variables (h) that describe the binding configuration can be used in the model, such as the particular geometric configuration m of the amino acids in the groove of the MHC molecule obtained from the available crystal structures. To predict MHC binding, a model $E(s,e,h)$ can be used, where s denotes a particular MHC allele, and e denotes a particular peptide, such that if the settings of h are provided, the model $E(s,e,h)$ can produce, for instance, a good estimate of the binding energy for the pair s,e. Such a model is in contrast to approaches to MHC binding in which the settings of h (e.g., the alignment) are provided by a separate routine unrelated to the model. The model $E(s, e, h)$ can be any suitable model including but not limited to a physics-based model and can be used to predict any suitable type of binding information such as a binding energy, a binary binding event (e.g., binder or not binder, epitope or not an epitope) or a binding probability (e.g., probability that the peptide is a binder or probability that the peptide is an epitope).

The states $E(s, e, h)$ of a MHC-peptide complex can be indexed by h with a partition function $$Z = \sum_h e^{-E(s,e,h)}.$$

In the example of a binding energy predictor, the free energy per particle of the system of particles is $F = -\log Z$, where the kT factors are omitted, as the reported measured binding energies are dimensionless log IC50 values. The measured binding energy log IC50 can be modeled as:

$$E(s, e) = -\log \sum_h e^{-E(s,e,h)} \quad (1)$$

For the case of a shift as the hidden variable h=l, if the assumption is that k amino acids are in the pocket, the energy of a particular configuration $E(s,e,l)$ can be derived from a model $E_{mod}(s,e)$ that does not address peptide shifts and that requires e to be a known k-mer sitting in the MHC groove such that $E(s,e,l)=E_{mod}(s,e_{l:l+k-1})$. Models of binding given a known alignment that can be used include most previous MHC I and MHC II binding models (e.g. pssm, logistic regression, support vector machine, motif search), some of which may have to be retrained in this new context. An example of retraining is described below in the context of an adaptive double-threading model in which h=(l,m) is the hidden variable using an EM-like learning algorithm that can fit the parameters of the model.

The variable peptide alignment in the groove can be treated as a distribution over possible alignments that is effectively determined by the model's energy predictions rather than by the fit of these predictions to the energy data. This means that the proper alignment can be inferred not only in training, but also in testing on new peptides for which the true (measured) binding energy is not provided to the predictor. For the case of a binding energy predictor, since the energy in equation (1) is dominated by the minimum energy state E(s,e,h), the preferred alignments will have lower energy, rather than better fit to the data.

The binding energy model can be based on the geometry of MHC-peptide complexes (e.g., threading approach) and can include learnable parameters that are estimated from the experimental data. Assuming that energy is additive, and that the pairwise potentials depend only on the amino acids themselves (rather than on their context in the molecule) the energy becomes a sum of pairwise potentials taken from a symmetric 20×20 matrix of pairwise potentials between amino acids. These parameters can be computed based on the amino acid binding physics or from statistical analyses of amino acid pair contact preferences. Various pairwise potentials have been described in the literature and using different pairwise potentials can yield different energy predictions.

To model MHC I-peptide binding, the binding energy can be estimated as (see Nebojsa Jojic, Manuel Reyes-Gomez, David Heckerman, Carl Kadie, and Ora Schueler-Furman, "Learning MHC I Peptide Binding," Bioinformatics, 2006 22: e227-e235):

$$E(m, s, e) \approx \sum_i \sum_j w_{i,j}^m \phi_{s_i,e_j} h(d_{i,j}^m), \quad (2)$$

where i is a sequence position in the MHC molecule having sequence s, j is a sequence position in the peptide having sequence e, m indexes the known 3-D structures, $w_{i,j}^m$ are learnable MHC-specific weights, $\phi_{s_i,e_j}$ are learnable pairwise contact potentials, $d_{i,j}^m$ is the distance between the i-th amino acid of the MHC molecule and the j-th amino acid of the peptide in the m-th known 3-D structure and h is a learnable soft threshold function. The learnable parameters serve to correct for the drastic approximations in the original threading approach by absorbing the errors of the model assumptions.

The distances $d_{i,j}^m$ are obtained from the 3-D structural data. The structural data can be, for instance, the 3-D coordinates of the amino acids of an MHC-peptide complex obtained by crystallography. A distance $d_{i,j}^m$ can be, for instance, the distance between an atom in the side chain of the i-th amino acid in the m-th MHC molecule and any atom in the j-th amino acid in the peptide. Even though the structure information d is inferred from a known binding configuration of a particular peptide-MHC I combination, substituting a different peptide of the same length (or even another MHC molecule) in the above equations still lead to a reasonable estimate of the binding energy for the new MHC-peptide combination. This is because relative positions and the basic chemistry of the amino acid-amino acid interactions are fixed. Light changes over different geometries of peptide-groove configurations (indexed by m) have a small but measurable effect on the accuracy of the model.

Traditional threading models employ a hard step function h(d) given by:

$$h(d) = \begin{cases} 1, & d \leq d_{thr} \\ 0, & d > d_{thr} \end{cases}$$

where $d_{thr}$ is a threshold distance. If the i-th amino acid of the MHC molecule and the j-th amino acid of the peptide are not at least as close the threshold distance, the amino acids do not contribute to the binding energy E. The parameter $d_{thr}$ is typically hand chosen to be about 4-4.5 Å. A threading model can be made more robust to slight variations in geometry by using a soft step function (e.g., sigmoid) that has a learnable softness of the step. This makes the predictor more robust because this eliminates the problem of turning off the contribution to the energy prediction of those amino acid pairs whose distance is close to the threshold but slightly above the threshold (as can occur with the hard step function). The learnable weights and contact potentials can be estimated together with the threshold and the softness of the step. One example of such a learnable soft step function is:

$$h(d)=1-(1/(1+e^{-A*(d_{i,j}^m-d_{thr})}))$$

where A is a parameter that determines the softness of the step function, $d_{thr}$ is the threshold distance and $d_{i,j}^m$ is the distance between the i-th amino acid of the MHC molecule and the j-th amino acid of the peptide in the m-th 3-D structure. The learnable parameters A and $d_{thr}$ can be estimated using machine learning algorithms designed to minimize the error between the predicted energies and the true energies (e.g., gradient descent).

The success of the previous work on MHC I binding energy prediction indicates that this main assumption holds well for MHC I molecule (see Nebojsa Jojic, Manuel Reyes-Gomez, David Heckerman, Carl Kadie, and Ora Schueler-Furman, "Learning MHC I Peptide Binding," Bioinformatics, 2006 22: e227-e235). The same basic modeling strategy used for MHC I binding can be used for modeling MHC II binding with one very important difference—while the fixed chemistry of the amino acid interactions and the fixed overall geometry of the MHC molecule are still relatively mild assumptions, the fixed relative position of the peptide is a gross over-approximation. Thus, a model of MHC II binding can account for variable positions of the peptide. By way of example, to estimate the energy of the binding configuration for a particular shift l, the following model threading model can be used:

$$E(m, s, e, \ell) \approx \sum_i \sum_{j=1+\ell}^{N+\ell} w_{i,j-\ell}^m \phi_{s_i,e_j} h(d_{i,j-\ell}^m). \quad (3)$$

In order to fit the model to experimental binding essays, the total affinity of the peptide can be expressed by summing over all the binding configurations. The experimental binding energy is usually reported in terms of an IC50 value that approximates the dissociation constant. The energy is assumed to be proportional to the negative log of this value, and so energy estimators are typically trained on the $E = -\log n_{IC50}$ values. When many copies of the same longer peptide are mixed with many copies of the same MHC class II molecule, binding configurations with all different shifts l may form. Therefore, according to equation (1), the two unknown variables that meaningfully affect the energy used in equation (3) can be summed:

$$E(s, e) = -\log \sum_{m,\ell} e^{-E(m,s,e,\ell)}. \quad (4)$$

As in the case of the MHC I model in equation (2), the variable m represents the geometry of the configuration of the MHC molecule and the bound portion of the peptide in the groove and influences the energy estimate through the distance matrix $d_{i,j}^m$. Since the variability in the binding configurations of the groove is low, the influence of variable m is existent, but mild. In the case of MHC II molecules, this variability has a much smaller effect on the energy estimate than the shift variable l such that upon 3D alignment of different MHC structures, the relative positions of molecules close to the binding grooves change very little. While the slight geometry changes in the groove have an effect on the prediction, the shift variable l influences the prediction much more dramatically as it alters the predicted amino acid composition of the peptide's segment sitting in the groove.

Short inspection (or simulation) of equation (4) reveals that the energy estimate is dominated by the state (m,l) with the smallest energy. However, as is explained below, it is typically dangerous to assume that the observed energies are equal to the minimum among the estimated energies for different states (m,l). This is because the predictors are inherently noisy, and the more states that are considered and the more predicted variability across the states, the more likely it becomes that the wrong minimum energy state will be picked with a dramatically wrong predicted energy value. Taking more states into account in the estimate, on the other hand will lead to more robust estimates.

In the training and testing procedures described below, the data is given in a form of a list of triples each consisting of an MHC II sequence s, a peptide sequence e and the measured binding energy E(s,e). During training, the model parameters w, φ, $d_{thr}$, A that minimize the error of approximation in equation (4) are determined. Any suitable optimization or search algorithms can be used to estimate the parameters from the experimental data. Since the error of approximation of equation (4) depends on the parameters in a highly nonlinear way, auxiliary variables can be introduced for each training case in order to simplify the optimization criterion into a simple quadratic form. This can be accomplished using an EM-style iteration of the parameter optimizations step with re-estimation of the case-specific auxiliary variables.

To derive the algorithm, an auxiliary probability distribution over states q(m,l), $0 \leq q(m,l) \leq 1$, $\Sigma_{m,l} q(m,l) = 1$ can be introduced. Since log is a concave function, this yields:

$$E(s, e) = -\log \sum_{m} \sum_{\ell=1}^{N-8} q(m, \ell) \frac{e^{-E(m,s,e,\ell)}}{q(m, \ell)} \geq -$$

$$\sum_{m} \sum_{\ell} q(m, \ell) \log \frac{e^{-E(m,s,e,\ell)}}{q(m, \ell)}$$

-continued $$= \sum_{m} \sum_{\ell} q(m, \ell) E(m, s, e, \ell) +$$

$$\sum_{m} \sum_{\ell} q(m, \ell) \log q(m, \ell).$$

Since for a given state m,l, the energy depends linearly on each subset of model parameters ω and φ, this bound on the energy is also bi-linear in terms of model parameters and an iterative linear regression can be used to minimize the approximation error. The above bound is true for any auxiliary probability distribution q, but it becomes tight (exact equality is accomplished) when:

$$q(m, \ell) = \frac{e^{-E(m,s,e,\ell)}}{\sum_{m,\ell} e^{-E(m,s,e,\ell)}}. \quad (5)$$

In other words, the distribution q is the exact distribution over states according to the energy model. This distribution depends on the sequence content of both the MHC molecule s and the peptide e, and so it can be recomputed for each training or test case. This distribution is not treated as a distribution over a variable with mutually exclusive and exhaustive states, but rather as population frequencies in the thermodynamics sense. In the former case, the hidden shift variable is inferred from a given binding energy, and in prediction, energies of different possible shifts would be averaged. In the latter case, the distribution over shifts depends on the predicted energies for individual shifts, and not on the observed energies, and so can be equally used in training and testing.

To learn the model parameters, the configuration inference step can be iterated with re-estimation of model parameters. Such an iterative learning algorithm can include the following steps:

Initialize model parameters (e.g., set all weight w to one, $d_{thr}$ and A so that the step function h is smooth and has a larger threshold, e.g. 6 or 7, and the φ matrix to either uniform or the one previously estimated for other purposes).

Initialize $q^t(m,l)$ to uniform for each training sample $e^t$, $s^t$, $E^t$ (t is the index for the training data).

Re-estimate the model parameters ω, φ, $d_{thr}$, A so that $$\sum_{t} (E(e^t, s^t) - E^t)^2$$

is minimized, where:

$$E(e^t, s^t) = \sum_{m,\ell} q^t(m, \ell) E(m, s^t, e^t, \ell) + \sum_{m,\ell} q^t(m, \ell) \log q^t(m, \ell). \quad (6)$$

Since the model is linear in w and linear in φ, iterative linear regression to solve for one set of parameters at a time is efficient. Step function parameters $d_{thr}$, A can be updated every few steps by gradient descent.

Using the new parameters, re-estimate the distribution $$q^t(m, \ell) = \frac{e^{-E(m,s^t,e^t,\ell)}}{\sum_{m,\ell} e^{-E(m,s^t,e^t,\ell)}}. \qquad (7)$$

Iterate the last two steps until convergence.
The possible shifts are not considered as equally likely a priori, rather the possible shifts depend on the peptide and MHC sequences. Consequently, the distribution over states m,l can be determined both for training and testing peptides, and in prediction, the state energies are not averaged. Rather, the possible binding configurations are considered as an ensemble with population frequencies defined by q. It is also different form the LP approach discussed in the introduction, which tries to infer a single best alignment for each peptide in training.

The update of the position distribution given by equation (7) and the estimate of the energy given by equation (6) are highly sensitive to the errors in prediction due to the nonlinearity of estimating the equivalent energy by summing over all configurations as in equation (4). This can cause local minima problems for as the parameters, and therefore the predictions, are less reliable in the early iterations of learning. For instance, assuming the total number of different shifts l is 10, and that the true binding energy for fake MHC-peptide configurations $E_l$ are drawn randomly from a uniform distribution on the interval [0,10], total binding energies can be computed according to $$E_{true} = -\log \sum_l e^{-E_l}$$

for 100 such configurations. Then incorporating an auxiliary temperature parameter:

$$E_{estimate} = -T\log \sum_\ell e^{-\frac{\tilde{E}_\ell}{T}}, \qquad (8)$$

where $\tilde{E}_l = E_l + v_l$, and $v_l$, a random variable drawn from a zero mean Gaussian distribution with some variance $\sigma^2$, simulates a modeling error. The choice of the auxiliary temperature parameter T>1 leads to smoothing of the energy estimate because by reducing the differences between the energies of different states, it becomes possible for more states to significantly influence the estimate. This is potentially useful as the wrong state may have the lowest energy due to the prediction errors and the state with the lowest energy dominates the estimate at T=1. For larger parameter T, the lowest energy state would contribute more to the estimate of the energy, but the other states would contribute, as well.

FIG. 1 shows how well the tempered prediction $E_{estimate}$ using the noisy predictions $E_l$ correlate with the true energies $E_{true}$ under the assumption that the measurement procedure which would in practice provide a direct measurement of $E_{true}$ is perfect and that a potential inability of a predictor to match it is only due to the predictor's errors in predicting the binding energy of the groove-peptide segment configurations for different shifts. In particular, FIG. 1 shows for different levels of error variance $\sigma^2$ how the Spearman correlation factor between $E_{true}$ and $E_{estimate}$ varies with the temperature T and that a rise in modeling error $\sigma^2$ can, to some extent, be absorbed by raising temperature factor T.

Adding the temperature factor T into equation (4) leads to the following change in equations (6) and (7):

$$E(e^t, s^t) = \sum_{m,\ell} q^t(m, \ell) E(m, s^t, e^t, \ell) + T \sum_{m,\ell} q^t(m, \ell) \log q^t(m, \ell) \qquad (9)$$

$$q^t(m, \ell) = \frac{e^{-\frac{E(m,s^t,e^t,\ell)}{T}}}{\sum_{m,\ell} e^{-\frac{E(m,s^t,e^t,\ell)}{T}}}. \qquad (10)$$

During training, rather than annealing the temperature according to some fixed training schedule, the optimal temperature parameter is searched for after every few updates of the model parameters. Upon convergence of all model and auxiliary parameters, the temperature typically settles to a value close to 1, which may indicate that the physical measurement errors are higher than the modeling errors.

By way of another example, a learning algorithm that treats the possible shifts as equally likely a priori can be utilized to train the model. Such a learning algorithm can infer the posterior distribution over geometric configurations by similarity of the measured energy to the energy of the configuration according to the model, for instance, it would use a probability distribution given by:

$$q^t(m, \ell) = \frac{e^{-f(E(s^t,e^t),E(m,s^t,e^t,\ell))}}{\sum_{m,\ell} e^{-f(E(s^t,e^t),E(m,s^t,e^t,\ell))}} \qquad (11)$$

Function $f$ captures the similarity between the measured energy E(s,e) and the energy predicted for a given geometric configuration (m,l). If the shift is determined strictly by thermodynamic considerations, then $f$ is set to y/T. Equation (10) above is equation (11) with $f$=y/T. If the shift is determined strictly by some external process, then $f$ is set to $(x-y)^2/\sigma^2$ where $\sigma^2$, where is the standard deviation of the Gaussian noise, if such noise is assumed. Furthermore, a nonuniform, but still sequence and peptide independent, preference for certain configurations can be expressed in the shape of a prior distribution p(m,l) and in that case the equation for q is:

$$q^t(m, \ell) = \frac{p(m, \ell) e^{-f(E(s^t,e^t),E(m,s^t,e^t,\ell))}}{\sum_{m,\ell} p(m, \ell) e^{-f(E(s^t,e^t),E(m,s^t,e^t,\ell))}} \qquad (12)$$

During the learning procedure described above, distribution p(m,l) can be re-estimated according to:

$$p(m, \ell) = \frac{1}{n} \sum_{t=1}^{n} q^t(m, \ell), \qquad (13)$$

where n is the number of training samples.

By way of yet another example, since the binding energy is proportional to the negative log of a probability, the predictor E can predict probabilities, such as the probability a peptide is a binder or the probability a peptide is an epitope. To predict a probability of an epitope, the model can be, for instance, trained on T-cell epitope data. For instance, one alternative to using the described threading model to predict binding information is to use an epitope probability estimator based on a logistic regression model. To use probability estimators p(s, e), where p represents the probability that e is an epitope for the MHC molecule described by sequence s in the equations described above, the following substitution can be made:

$$E(s,e,l) = -\log p(s,e,l)$$

where $$p(s,e,l) = p(s,e_{l:l+k})$$

and k is the length of the part of the peptide deemed important to binding (e.g., length of an epitope, which is usually from about 8 to about 11 amino acids, typically around 9 amino acids).

Experimental Data

The complete set of MHC II structures that contain an epitope of at least seven amino acids were obtained from the Protein Data Bank. The resulting set consisted of 12 HLA-DR and 3 HLA-DQ alleles. These structures are used as exemplars m of the groove structures in the experiments described below. Although data for the MHC II HLA-DP alleles are missing from this set, these alleles share relatively high sequence similarity with HLA-DR alleles. To evaluate the prediction accuracy, the methods were used both as an epitope predictor and a binding energy predictor and tested on the available epitope and energy data. In addition to comparisons with existing techniques for epitope prediction, the ability of the Shift Invariant Double Threading (SIDT) model to assist in association studies in immunology was analyzed.

Energy and Epitope Prediction Experiments on Published Data Sets and Comparisons with Other Methods Using the MHCPEP Dataset The MHCPEP data set has been used by others to evaluate the performance of the MHC II binding predictors DistBoost and RANKPEP. Following the procedures described in Hertz T, Yanover C., "PepDist: A New Framework for Protein-Peptide Binding Prediction Based on Learning Peptide Distance Functions," BMC Bioinformatics, 2006 Mar. 20; 7 Suppl 1:S3 and Reche P A, Glutting J P, Zhang H, Reinherz E L, "Enhancement to the RANKPEP Resource for the Prediction of Peptide Binding to MHC Molecules using Profiles," Immunogenetics, 2004 September; 56(6):405-19, Epub 2004 Sep. 3, the contents of the MHCPEP database were downloaded in order to compare the relative performance of our method. Unlike these published procedures, the SIDT method does not require an alignment step and therefore this step was omitted. The data obtained were peptide sequences paired with MHC alleles and binding affinities with all peptides classified as low binders or with unknown residues at some position removed from the dataset. All peptides from non-human MHC alleles also were removed from the dataset (although the method can be applied to these as well). This resulted in 1265 peptides from 17 MHC II alleles.

The SIDT method was compared to DistBoost and RANKPEP by replicating the exact same experimental setup. The MHCPEP dataset described above was used as the set of positive binders. Non-binders were taken from random protein sequence from the SwissProt database so that there were twice as many non-binders as binders per allele. Training was performed using half of the binders for each allele with twice as many non-binders. Testing was performed on the remaining set. Five-fold cross validation over the training set was used to find an optimal set of parameters and then the SIDT method was evaluated on the test set. This setup was repeated 10 times to measure average performance and standard deviation. ROC curves for the SIDT model were plotted and the AUC of the SIDT method was compared with the published results of RANKPEP and DistBoost. The SIDT method outperformed both DistBoost and RANKPEP on 15 out of the 17 data sets (p-value 0.00014 binomial) as shown in Table 1 below. The average AUC for the SIDT method was 0.87 compared to 0.78 for DistBoost and 0.71 for RANKPEP. In addition, the average standard deviation of the SIDT method was lower than either DistBoost or RANKPEP, 0.04 compared to 0.044 and 0.05, which indicates that the SIDT method is as robust or better than either DistBoost or RANKPEP.

TABLE 1

Comparison of RANKPEP, DistBoost, and the Shift Invariant Double Threading (SIDT) method over the MHCPEP data set. Best values shown in bold font. Columns A and B for DistBoost refer to training without and with negative constraints. Columns A and B for RANKPEP refer to PSSMs constructed using PROFILEWEIGHT and BLK2PSSM.

| Allele | $RANKPEP_A$ | $RANKPEP_B$ | $DistBoost_A$ | $DistBoost_B$ | SIDT | # |
|---|---|---|---|---|---|---|
| QA10501 × 0201 | 0.87 | 0.88 | 0.93 | 0.93 | 0.87 | 31 |
| QA10301 × 0302 | 0.7 | 0.7 | 0.75 | 0.77 | 0.87 | 52 |
| PA10201 × 0901 | 0.8 | 0.88 | 0.75 | 0.74 | 0.88 | 18 |
| RB10101 | 0.74 | 0.75 | 0.81 | 0.8 | 0.87 | 188 |
| RB10102 | 0.72 | 0.72 | 0.9 | 0.83 | 0.91 | 21 |
| RB10401 | 0.68 | 0.6 | 0.71 | 0.73 | 0.87 | 321 |
| RB10402 | 0.7 | 0.72 | 0.74 | 0.69 | 0.88 | 72 |
| RB10405 | 0.76 | 0.82 | 0.86 | 0.86 | 0.89 | 64 |
| RB10404 | 0.7 | 0.61 | 0.74 | 0.7 | 0.84 | 44 |
| RB10701 | 0.71 | 0.72 | 0.79 | 0.76 | 0.89 | 81 |
| RB10901 | 0.8 | 0.78 | 0.89 | 0.91 | 0.97 | 39 |
| RB11101 | 0.57 | 0.54 | 0.76 | 0.73 | 0.85 | 124 |
| RB11501 | 0.61 | 0.6 | 0.73 | 0.75 | 0.87 | 35 |
| RB50101 | 0.83 | 0.81 | 0.83 | 0.8 | 0.87 | 52 |
| RB10801 | 0.52 | 0.52 | 0.67 | 0.65 | 0.84 | 42 |
| RB11104 | 0.91 | 0.92 | 0.87 | 0.88 | 0.83 | 29 |
| RB10301 | 0.54 | 0.52 | 0.54 | 0.62 | 0.83 | 52 |
| AVERAGE | 0.72 | 0.71 | 0.78 | 0.77 | 0.87 | 74.4 |

Energy and Epitope Prediction Experiments on Published Data Sets and Comparisons with Other Methods Using the MHCBench Dataset The MHCBench dataset was constructed for the purpose of evaluating MHC II binding predictors. In order to evaluate the relative performance of the SIDT method, the training and testing procedures described in Nielsen M, Lundegaard C, Worning P, Hvid C S, Lamberth K, Buus S, Brunak S, Lund O, "Improved Prediction of MHC Class I and Class II Epitopes Using a Novel Gibbs Sampling Approach,"Bioinformatics, 2004 Jun. 12; 20(9):1388-97, Epub 2004 Feb. 12 and Murugan N, Dai Y, "Prediction of MHC Class II Binding Peptides Based on an Iterative Learning Model," Immunome Res., 2005 Dec. 13; 1:6 were followed. The set of HLA-DRB1*0401 binding peptides that were added before 1999 were obtained from the SYFPEITHI database. The procedure of Nielsen et al. does not require negative training examples, so the example of Murugan et al. was followed and the HLA-DRB1*0401 non-binders from the MHCBN database were added. Peptides that have a hydrophobic residue in the first position were removed. Peptides that were more than 75% alanine also were removed. This resulted in a dataset of 462 binding and 177 non-binding peptides for use as the training dataset. Since the SIDT method also has the capability to incorporate information from other alleles during training, another training data set consisting of the dataset described above with the addition of non HLA-DRB1*0401 peptides contained at MHCBN was created. All peptides overlapping the test data with alignment over 90% were removed leaving a set of 2997 peptides.

The test datasets used by Nielsen et al. and Murugan et al. consist of the 8 datasets described in MHCBench and the datasets from Southwood S, Sidney J, Kondo A, del Guercio M F, Appella E, Hoffman S, Kubo R T, Chesnut R W, Grey H M, Sette A, "Several Common HLA-DR Types Share Largely Overlapping Peptide Binding Repertoires," J Immunol. 1998 Apr. 1; 160(7):3363-73 and Geluk A, van Meijgaarden K E, Schloot N C, Drijfhout J W, Ottenhoff T H, Roep B O, "HLA-DR Binding Analysis of Peptides from Islet Antigens in IDDM," Diabetes, 1998 October; 47(10):1594-601. In the MHCBench dataset, any peptide with a non-zero value was considered a binder and for the other data sets, any peptide with affinity of less than 1000 nM was considered a binder. All others were considered non-binders. Since there is a significant overlap between the peptides in the training and test data sets, any peptide with >90% sequence identity to a peptide in the training set was removed.

Five-fold cross validation over the training set was performed to estimate the optimal set of parameters for the SIDT model. ROC curves were generated for each test set and the AUC was computed for comparison with the published results of Linear Programming, Gibbs, and TEPITOPE methods. The results are shown in Table 2 below. In addition, training was performed on another training data set which contained peptides from other alleles to show how the SIDT method can incorporate other data to improve performance (indicated by SIDT* in Table 2 below). The SIDT method has a higher average ROC than any of the other methods and it is further improved by adding non DRB1*0401 alleles to the training set. The SIDT method outperformed the other methods on 8 out of 10 data sets (pvalue<0.017 binomial). In training the SIDT model, a cutoff of $e^{6.2}$ for good versus bad binders is used rather than the 1000 nM cutoff used for the Southwood et al. and Geluk et al. datasets used for the test data. Using the cutoff of $e^{6.2}$ improves the SIDT performance, but cannot be compared with the other methods since the training set would be different.

TABLE 2

Performance of the Shift Invariant Double Threading (SIDT) method, the Gibbs sampler, TEPITOPE, and the Linear Programming (LP) method over 10 homology reduced data sets. SIDT* is the SIDT method trained with additional data for different alleles in order to demonstrate the ability of the SIDT method to take advantage of information across alleles. Set1–Set5b are the 8 datasets from MHCBench above and Geluk and Southwood are the datasets from those references above.

| Method | Set1 | Set2 | Set3a | Set3b | Set4a | Set4b | Set5a | Set5b | Geluk | Southwood | Average |
| --- | --- | --- | --- | --- | --- | --- | --- | --- | --- | --- | --- |
| SIDT | 0.76 | 0.71 | 0.73 | 0.79 | 0.77 | 0.72 | 0.71 | 0.79 | 0.78 | 0.61 | 0.737 |
| SIDT* | 0.75 | 0.73 | 0.72 | 0.74 | 0.77 | 0.73 | 0.83 | 0.85 | 0.78 | 0.69 | 0.759 |
| Gibbs | 0.68 | 0.66 | 0.6 | 0.69 | 0.67 | 0.68 | 0.59 | 0.59 | 0.69 | 0.88 | 0.673 |
| Tepi | 0.6 | 0.65 | 0.6 | 0.7 | 0.59 | 0.66 | 0.66 | 0.68 | 0.66 | 0.49 | 0.629 |
| LP2 | 0.67 | 0.7 | 0.67 | 0.76 | 0.65 | 0.7 | 0.73 | 0.76 | 0.66 | 0.84 | 0.714 |

Generalizing to New Alleles

Although some techniques have some level of generalization (such as TEPITOPE which learns individual binding pockets), most models do not. In contrast, after training the SIDT model any MHC sequence can be threaded onto a structure and used for binding prediction. Therefore, the SIDT can predict peptide binding for alleles with little or no experimental data. For MHC I molecules there are hundreds of alleles. MHC II molecules are polymers of two different molecules called the alpha and beta chains. For instance, HLA-DQ has several hundred alpha and beta chains with thousands of possible combinations, each of which bind different peptides. Thus, since peptide binding experiments are currently costly and time consuming, the ability to predict binding for unseen alleles is an extremely useful feature of the SIDT method.

The Immune Epitope Database and Analysis Resource (IEDB) is a meticulously curated database of peptide binding data. This resource maintains a hand curated list of epitopes and carries continuous IC50 values. The complete IEDB MHC and T-cell binding data was obtained from the IEDB. Peptides from before 1993 and any peptide marked as a good binder with an IC50 of greater than 3000 and any peptide marked as a non-binder with IC50 less than 500 were removed. In order to have an equal number of binding and non-binding peptides in each allele set, random human peptides from SwissProt were added until each allele was balanced.

Figure 2:
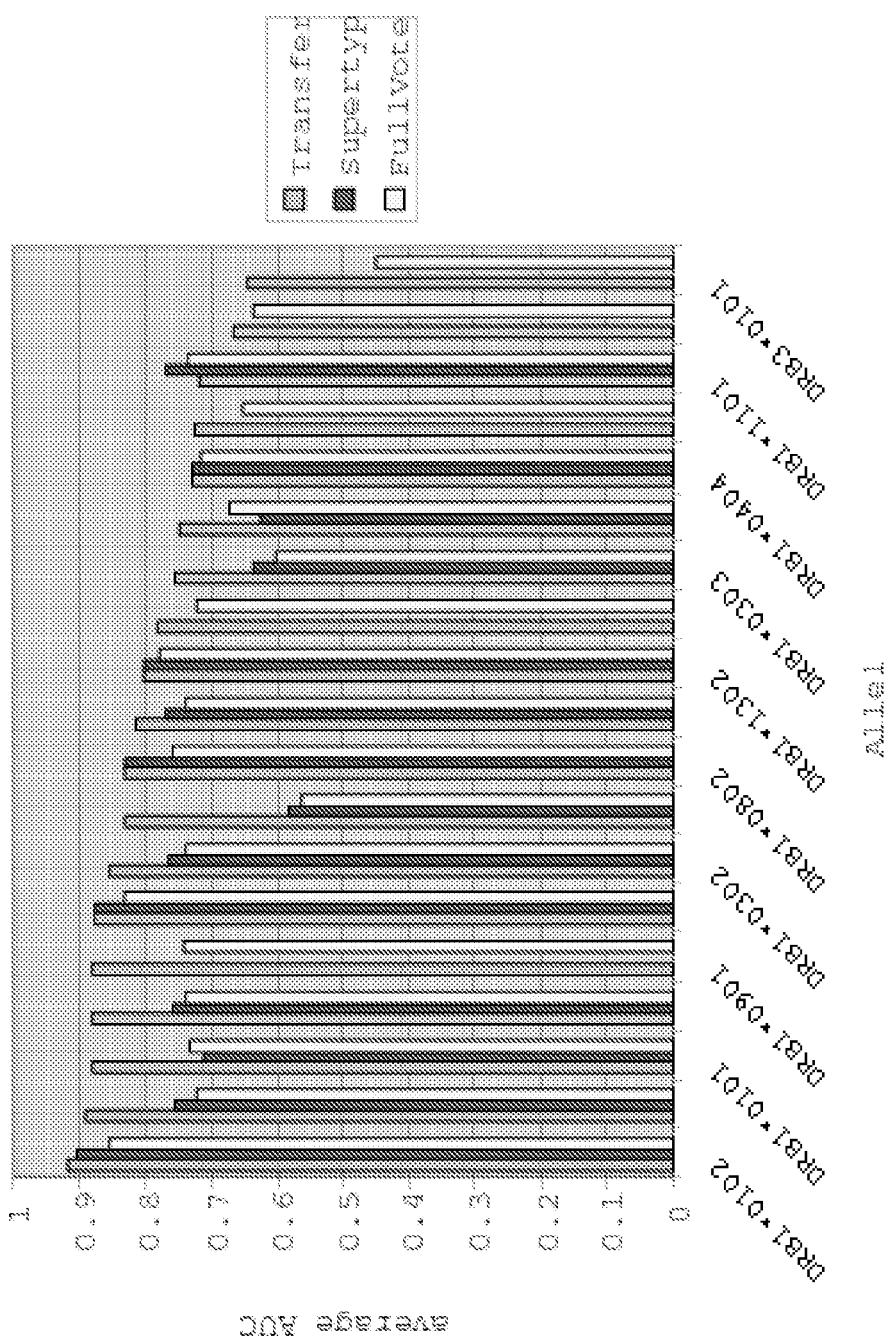
FIG. 2 is a graph showing the capability of the Shift Invariant Double Threading (SIDT) method to generalize to allow for epitope prediction for alleles not found in the training set. This capability allows the SIDT method to be applied to a much larger set of MHC molecules. The graph shows the significantly greater predictive power of the SIDT method over two voting based mechanisms for binding across alleles.

Using this dataset, transfer datasets were created by removing all epitopes of each allele in turn. For each of these datasets, the SIDT model was trained using five-fold cross validation to estimate the optimal parameters. The MHC sequence of the allele that was left out of the transfer set was threaded onto the structure of the allele that had the closest sequence. The SIDT model was tested using this combination of the sequence and structure over all of the alleles from the dataset. Since there is significant overlap between peptides that bind to different alleles, the transfer results were compared to two different voting based methods for predicting binding of unseen alleles. The SIDT trained model was evaluated for all observed alleles in the training data over the set of peptides of the unobserved allele. A peptide was called a binder if the majority of the alleles called it a binder. In another voting setup, a peptide was called a good binder if a majority of the alleles in the supertype of the left out allele called it a good binder. ROC curves for the performance of each method were plotted and the average AUC was calculated. The results are show in FIG. 2. As shown in FIG. 2, the SIDT method significantly outperforms either voting mechanism (p-value<0.00001 binomial). The SIDT is able to predict peptide binding for MHC II alleles after having learned over both alpha and beta chains, a single alpha or beta chain, or without any previous exposure to either chain of the allele.

greater than that predicted for MBP 85-99 (for polymers 1, 2, and 3 respectively). When 20 random SwissProt proteins of equivalent length were used, only 10 stronger binders were identified. These results show that the SIDT method predicts the potential therapeutic uses of these copolymers.

Others have examined the properties of the copolymers and synthesized non-random peptides of length 15 (see Stern J N, Illes Z, Reddy J, Keskin D B, Fridkis-Hareli M, Kuchroo V K, Strominger J L, "Peptide 15-mers of defined Sequence that Substitute for Random Amino Acid Copolymers in Amelioration of Experimental Autoimmune Encephalomyelitis," Proc Natl Acad Sci U.S.A., 2005 Feb. 1; 102(5):1620-5, Epub 2005 Jan. 21). Three of these J2, J3, and J5 were experimentally found to suppress MBP 85-99 binding with the relative strength of suppression J5>J3>J2. The SIDT method was run over each of these 15 amino acid long peptides and all three had predicted binding energies lower than MBP 85-99 (indicating that they form stronger bonds). Furthermore, the order

TABLE 3

Description of the datasets. Trn is the training set used for the MHCBench test set. Trn2 is the same training set with the addition of peptides belonging to different alleles. Set1–Set5b are the 8 datasets from MHCBench above and Geluk and Southwood are the datasets from those references above.

|  | Set1 | Set2 | Set3a | Set3b | Set4a | Set4b | Set5a | Set5b | Southwood | Geluk | Trn | Trn2 | PEP |
|---|---|---|---|---|---|---|---|---|---|---|---|---|---|
| Bind | 248 | 161 | 151 | 128 | 120 | 120 | 65 | 47 | 19 | 15 | 462 | 1782 | 1037 |
| Non | 283 | 255 | 204 | 197 | 283 | 255 | 45 | 37 | 80 | 6 | 177 | 121 | 2074 |
| Total | 531 | 416 | 355 | 325 | 403 | 375 | 110 | 84 | 99 | 21 | 639 | 2997 | 3111 |

Myelin Binding Studies

The SIDT binding predictor was run using data from laboratory experiments that determined whether a particular MHC II allele correlates with an autoimmune disorder— multiple sclerosis (MS). This was done in order to determine if the predictions matched the results of the laboratory experiments and thus, to determine whether predictions can be used as an alternative to laboratory experiments. MS is caused by the auto-immune degradation of the nerve insulating material referred to as myelin, which disrupts signal passage through the nervous system and causes neurological problems. Studies have shown that the HLA-DR2 supertype is positively associated with MS. Myelin Basic Protein (MBP) has been shown to bind to the MHC II allele HLA-DRB1*1501 and thus, is a potential auto-antigen in the pathogenesis of MS. Notably, residues 85-99 of MBP have been shown experimentally to be an immunodominant epitope for HLA-DRB1*1501. Accordingly, peptides that can displace MBP 85-99 by competitively binding to the HLA-DRB1*1501 allele have therapeutic potential. Indeed, a drug that works by disrupting this binding has been approved to treat certain forms of MS and the evidence indicates that it can suppress relapse rates of certain forms of MS.

The SIDT method was run over the MBP using the HLA-DR2 allele HLA-DRB1*1501 and four potential binders were identified. Of these, the strongest signal was located at amino acid 91 of the MBP (which is within MBP 85-99). The aforementioned drug approved to treat MS and two other competitive binding peptides take the form of copolymers 1 poly(Y, E, A, K)n, 2 poly(F, Y, A, K)n, and 3 poly(V, W, A, K)n. These are peptide sequences of random combinations of each of the amino acids in the poly groups. The number of binders predicted to bind to HLA-DRB1*1501 were measured over 20 random peptides of each of these polymers. The results indicted that in 20 polymers of length 50, there were 60, 80, and 155 predicted binders with a binding strength of binding strength matched that of the relative levels of suppression. That is, J5 was the strongest binder followed by J3 and then J2.

Although the examples provided above have focused on particular models such as the threading approach, any suitable model can be made shift invariant. By way of example, a trained predictor $E(e,s)$ that predicts binding information (e.g., binding energy, binary binding event or binding probability) but is not shift invariant can be made shift invariant by computing:

$$q(\ell) = \frac{e^{-E(s,e,\ell)}}{\sum_{\ell} e^{-E(s,e,\ell)}}$$

and using q(l) to compute E(e,s):

$$E(e, s) = \sum_{\ell} q(\ell) E(s, e, \ell) + \sum_{\ell} q(\ell) \log q(\ell)$$

If the predictor has trainable parameter(s), it can be retrained using any suitable learning algorithm, such as the Expectation-Maximization style iterative learning algorithm described above.

Figure 3:
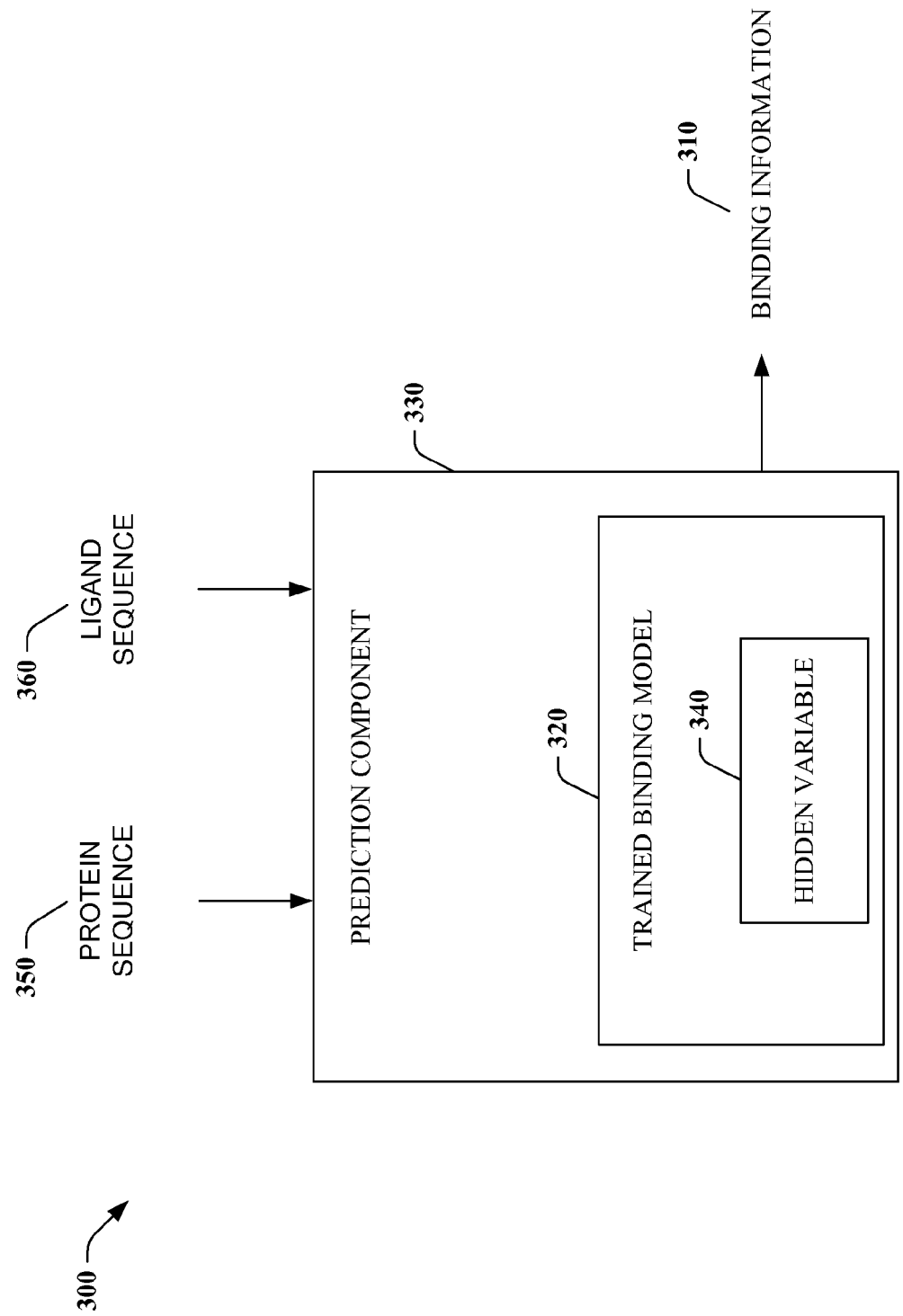
FIG. 3 is a block diagram of one example of a system for predicting binding information relating to the binding of a protein and a ligand.

FIG. 3 schematically illustrates one example of a system 300 for predicting binding information 310 (e.g., binding energy, binary binding event such as whether a peptide is a binder or is not a binder or a probability) relating to the binding of a protein (e.g., an MHC class II molecule or a synthetic molecule) and a ligand (e.g., a peptide of about 8-11 amino acids in length). The system 300 can be, for instance, a computer executed system such as one stored on computer-readable media. The system 300 can include a trained binding model 320 and a prediction component 330. The trained binding model 320 can have a hidden variable 340 representing an unknown alignment of the ligand with the protein at a binding site of the protein. The prediction component 330 can be configured to predict the binding information 310 by employing information about the protein's sequence 350, the ligand's sequence 360 and the trained binding model 320. The system 300 can be implemented by software or combinations of software and hardware and can be the same process executing on a single or a plurality of microprocessors or multiple processes executing on a single or a plurality of microprocessors.

The trained binding model 320 can be any suitable binding model such as those described above (e.g., a threading model or a model that is not structure-based). The trained binding model 320 can include any suitable parameters (e.g., MHC-specific weights, learnable contact potentials, learnable soft-step function). By way of example, the trained binding model 320 can be given by:

$$E(e, s) = \sum_{m,\ell} q(m, \ell) E(m, s, e, \ell) + T \sum_{m,\ell} q(m, \ell) \log q(m, \ell)$$

where the binding information $E(e,s)$ is a binding energy, T is a temperature parameter, m is a parameter related to a configuration of amino acids at the binding site of the protein, s is a parameter related to the protein's sequence, e is a parameter related to the ligand's sequence, l is the hidden variable representing the unknown alignment of the ligand at the binding site of the protein, $q(m,l)$ is given by:

$$q(m, \ell) = \frac{e^{-f(E(s,e), E(m,s,e,\ell))}}{\sum_{m,\ell} e^{-f(E(s,e), E(m,s,e,\ell))}}$$

and where $f$ is a function that captures a similarity between measured binding information and binding information predicted for a given alignment. The function $f$ can be given by $f=y/T$ or $(x-y)^2/\sigma^2$ where $\sigma^2$ is the level of noise.

The systems described above can be implemented in whole or in part by electromagnetic signals. These manufactured signals can be of any suitable type and can be conveyed on any type of network. For instance, the systems can be implemented by electronic signals propagating on electronic networks, such as the Internet. Wireless communications techniques and infrastructures also can be utilized to implement the systems.

Figure 4:
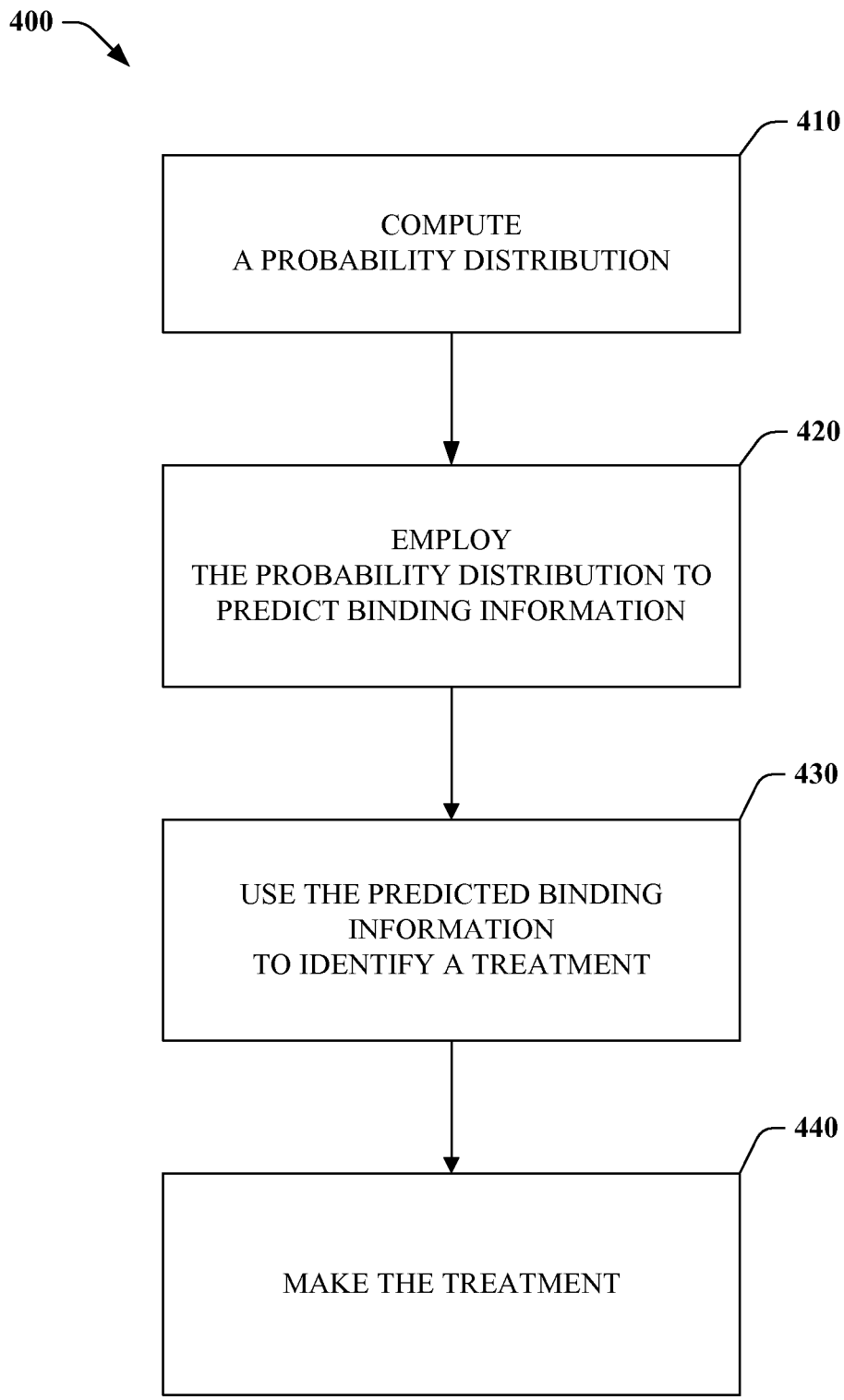
FIG. 4 is a flow diagram of one example of a method of making a treatment.

FIG. 4 a flow diagram of one example of a method 400 of making a treatment by utilizing predicted binding information about a protein (e.g., MHC molecule) and a ligand (e.g., an epitope or autoantigen). At step 410, a probability distribution relating to an alignment of the ligand when bound to the protein is computed. At step 420, the probability distribution is employed to predict binding information (e.g., binding energy, binary binding event or binding probability) about the protein and the ligand. At step 430, the predicted binding information is used to identify a treatment and at step 440, the treatment is made. By way of example, the treatment can be a drug that works by disrupting binding between an MHC molecule and an autoantigen such as a competitive inhibitor of the autoantigen (e.g., a peptide competitive inhibitor). The competitive inhibitor can be a naturally occurring molecule or a synthetic molecule. The treatment can be made in any suitable fashion such as by peptide synthesis techniques.

Any suitable techniques can be used to accomplish the steps 410, 420, 430 of the method such as those described above. For instance, computing the probability distribution relating to the alignment of the ligand when bound to the protein can be accomplished by computing:

$$q(m, \ell) = \frac{e^{-\frac{E(m,s,e,\ell)}{T}}}{\sum_{m,\ell} e^{-\frac{E(m,s,e,\ell)}{T}}}$$

where E is a binding energy, T is a temperature parameter, m is a parameter related to a configuration of amino acids at a binding site of the protein, s is a parameter related to the protein's sequence, e is a parameter related to the ligand's sequence and/is a hidden variable representing the alignment of the ligand when bound to the protein. By way of another example, employing the probability distribution to predict binding information about the protein and the ligand can be accomplished by computing:

$$E(e, s) = \sum_{m,\ell} q(m, \ell) E(m, s, e, \ell) + T \sum_{m,\ell} q(m, \ell) \log q(m, \ell).$$

Figure 5:
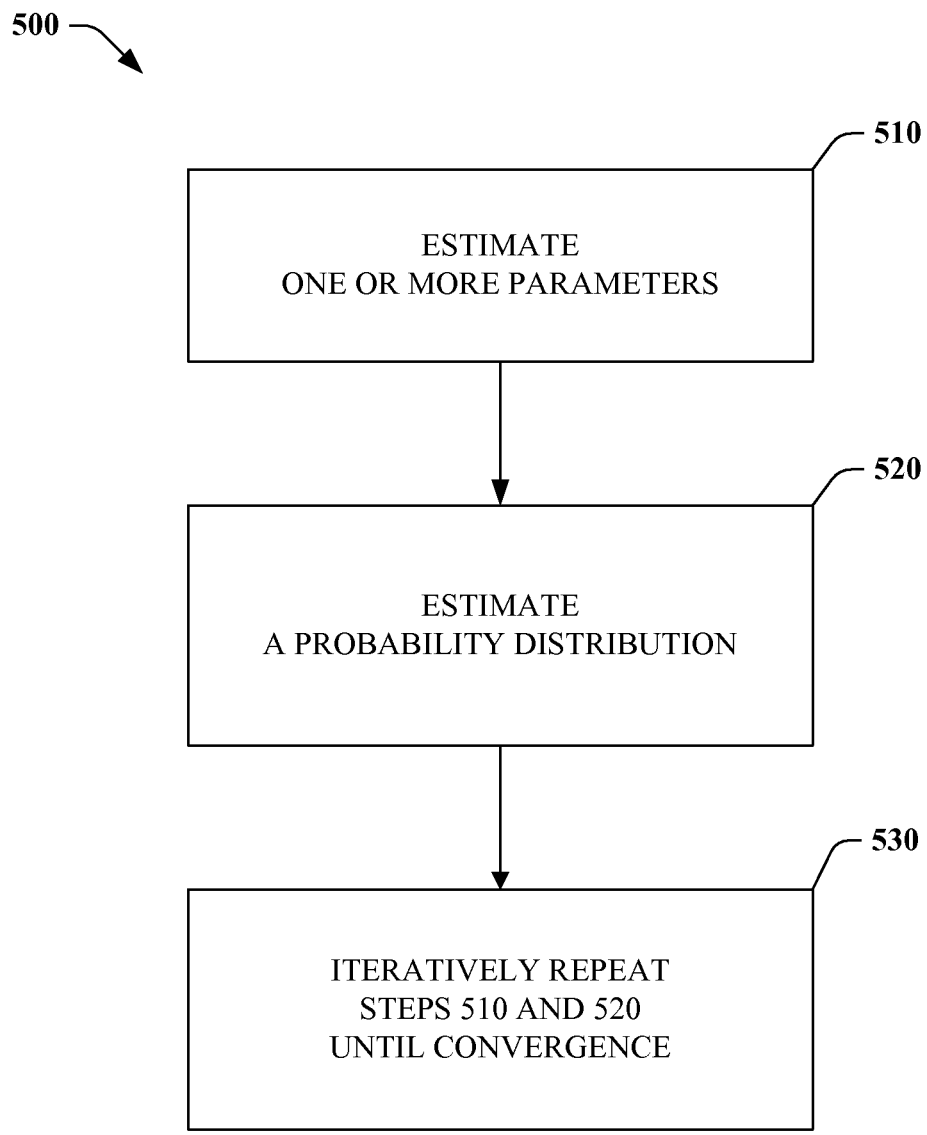
FIG. 5 is a flow diagram of one example of a method of generating a binding predictor.

FIG. 5 a flow diagram of one example of a method 500 of generating a binding predictor. The method 500 can be encoded by computer-executable instructions stored on computer-readable media. The binding predictor can be any suitable predictor such as those described above (e.g., a predictor to predict the binding of an MHC molecule and a peptide from about 8-11 amino acids in length, a shift invariant double threading predictor, etc.) and can predict any suitable binding information such as those described above (e.g., binding energy, binary binding event, binding probability, etc.). At step 510, one or more parameters of the binding predictor are estimated from training data. At step 520, a probability distribution that relates to a geometric configuration of a ligand bound to a protein can be estimated from the training data. Steps 510 and 520 are iteratively repeated until convergence as shown in step 530.

The steps 510 and 520 of the method 500 can be accomplished in any suitable manner such as those described above. For instance, the step of estimating the one or more parameters 510 of the binding predictor can be accomplished by estimating one or more parameters of an adaptive threading model using iterative linear regression, gradient descent or combinations thereof. By way of example, the adaptive threading model can be given by the equation:

$$E(m, s, e, \ell) \approx \sum_{i} \sum_{j=1+\ell}^{N+\ell} w_{i,j-\ell}^{m} \phi_{s_i, e_{j-\ell}} h(d_{i,j-\ell}^{m})$$

where $w_{i,j-\ell}^{m}$ are protein-specific weights, $\phi_{s_i, e_{j-\ell}}$ are pairwise contact potentials, $d_{i,j-\ell}^{m}$ are distances between the protein and the amino acids of the ligand, h is a trainable soft threshold function and l is a hidden variable that represents the geometric configuration of the ligand when bound to the protein. By way of another example, the step of estimating the probability distribution 520 can be accomplished by estimating $q'(m,l)$.

The methods can be implemented by computer-executable instructions stored on one or more computer-readable media or conveyed by a signal of any suitable type. The methods can be implemented at least in part manually. The steps of the methods can be implemented by software or combinations of software and hardware and in any of the ways described above. The computer-executable instructions can be the same process executing on a single or a plurality of microprocessors or multiple processes executing on a single or a plurality of microprocessors. The methods can be repeated any number of times as needed and the steps of the methods can be performed in any suitable order.

The subject matter described herein can operate in the general context of computer-executable instructions, such as program modules, executed by one or more components. Generally, program modules include routines, programs, objects, data structures, etc., that perform particular tasks or implement particular abstract data types. Typically, the functionality of the program modules can be combined or distributed as desired. Although the description above relates generally to computer-executable instructions of a computer program that runs on a computer and/or computers, the user interfaces, methods and systems also can be implemented in combination with other program modules. Generally, program modules include routines, programs, components, data structures, etc. that perform particular tasks and/or implement particular abstract data types.

Moreover, the subject matter described herein can be practiced with all computer system configurations, including single-processor or multiprocessor computer systems, mini-computing devices, mainframe computers, personal computers, stand-alone computers, hand-held computing devices, wearable computing devices, microprocessor-based or programmable consumer electronics, and the like as well as distributed computing environments in which tasks are performed by remote processing devices that are linked through a communications network. In a distributed computing environment, program modules can be located in both local and remote memory storage devices. The methods and systems described herein can be embodied on a computer-readable medium having computer-executable instructions as well as signals (e.g., electronic signals) manufactured to transmit such information, for instance, on a network.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing some of the claims.

It is, of course, not possible to describe every conceivable combination of components or methodologies that fall within the claimed subject matter, and many further combinations and permutations of the subject matter are possible. While a particular feature may have been disclosed with respect to only one of several implementations, such feature can be combined with one or more other features of the other implementations of the subject matter as may be desired and advantageous for any given or particular application.

In regard to the various functions performed by the above described components, computer-executable instructions, means, systems and the like, the terms are intended to correspond, unless otherwise indicated, to any functional equivalents even though the functional equivalents are not structurally equivalent to the disclosed structures. To the extent that the terms "includes," and "including" and variants thereof are used in either the specification or the claims, these terms are intended to be inclusive in a manner the same as the term "comprising." Furthermore, any use of the conjunctions "or" and "and" are intended to be non-exclusive. Accordingly, the claimed subject matter is intended to embrace all such alterations, modifications, and variations that fall within the spirit and scope of the appended claims.

What is claimed is:

1. A computer-implemented system for predicting binding information relating to a binding of a protein and a ligand, comprising the following computer components stored in one or more memory storage devices and executable by one or more processors:

a trained binding model comprising a hidden variable representing an unknown alignment of the ligand with the protein at a binding site of the protein, the trained binding model further comprising one or more parameters selected from a group Major Histocompatibility Complex (MHC)-specific weights, learnable contact potentials, and a learnable soft-step function;

the one or more parameters of the trained binding model being estimated based at least in part on machine learning algorithms to minimize an error between the predicted binding information and a true binding information;

a prediction component configured to predict the binding information by employing information about a protein's sequence, a ligand's sequence, and the trained binding model; and the trained binding model using a shift variable to influence predicting the binding information by altering a predicted amino acid composition.

2. The system of claim 1, wherein the trained binding model comprises a threading model.

3. The system of claim 1, wherein the trained binding model is given by:

$$E(e, s) = \sum_{m,\ell} q(m, \ell) E(m, s, e, \ell) + T \sum_{m,\ell} q(m, \ell) \log q(m, \ell)$$

where the binding information $E(e,s)$ is a binding energy, T is a temperature parameter, m is a parameter related to a configuration of amino acids at the binding site of the protein, s is a parameter related to the protein's sequence, e is a parameter related to the ligand's sequence, l is the hidden variable representing the unknown alignment of the ligand with the protein at the binding site of the protein, where an auxiliary probability distribution over states, $q(m,l)$ is given by:

$$q(m, \ell) = \frac{e^{-f(E(s,e),E(m,s,e,\ell))}}{\sum_{m,\ell} e^{-f(E(s,e),E(m,s,e,\ell))}}$$

and where f is a function that captures a similarity between measured binding information and binding information predicted for a given alignment.

4. The system of claim 3, wherein f is given by f=y/T, representing a factor over the temperature (T) if a shift is determined by thermodynamic considerations or representing an error variance is a level of noise if the shift is determined by at least one external process.

5. The system of claim 1, wherein the protein is a MHC class II molecule and the ligand is a peptide of about 8-11 amino acids in length.

6. The system of claim 5, wherein the MHC class II molecule is a synthetic molecule.

7. The system of claim 1, wherein the binding information is a probability.

8. A method of predicting binding information relating to a binding of a protein and a ligand, comprising:

under control of one or more processors configured with executable instructions:

representing an unknown alignment of a ligand with a protein at a binding site of the protein using a trained binding model, the trained binding model comprising one or more parameters selected from a group Major Histocompatibility Complex (MHC)-specific weights, learnable contact potentials, and a learnable soft-step function;

estimating the one or more parameters of the trained binding model based at least in part on machine learning algorithms to minimize an error between predicted binding information and a true binding information;

predicting the binding information by employing information about a protein's sequence, a ligand's sequence, and the trained binding model; and using a shift variable to influence the predicting of the binding information by altering a predicted amino acid composition.

9. The method of claim 8, wherein the trained binding model comprises a threading model.

10. The method of claim 8, wherein the trained binding model is given by:

$$E(e, s) = \sum_{m,\ell} q(m, \ell) E(m, s, e, \ell) + T \sum_{m,\ell} q(m, \ell) \log q(m, \ell)$$

where the binding information E(e,s) is a binding energy, T is a temperature parameter, m is a parameter related to a configuration of amino acids at the binding site of the protein, s is a parameter related to the protein's sequence, e is a parameter related to the ligand's sequence, l is the hidden variable representing the unknown alignment of the ligand with the protein at the binding site of the protein, where an auxiliary probability distribution over states, q(m,l) is given by:

$$q(m, \ell) = \frac{e^{-f(E(s,e),E(m,s,e,\ell))}}{\sum_{m,\ell} e^{-f(E(s,e),E(m,s,e,\ell))}}$$

and where f is a function that captures a similarity between measured binding information and binding information predicted for a given alignment.

11. The method of claim 10, wherein f is given by f=y/T, representing a factor over the temperature (T) if a shift is determined by thermodynamic considerations or representing an error variance is a level of noise if the shift is determined by at least one external process.

12. The method of claim 8, wherein the protein is a MHC class II molecule and the ligand is a peptide of about 8-11 amino acids in length.

13. The method of claim 12, wherein the MHC class II molecule is a synthetic molecule.

14. The method of claim 8, wherein the binding information is a probability.

* * * * *